US005205300A

United States Patent [19]

Hawkins et al.

[11] Patent Number: 5,205,300

[45] Date of Patent: Apr. 27, 1993

[54] METHOD FOR DETERMINING EFFECTIVENESS OF RELAXER TREATMENT

[75] Inventors: Geoffrey R. Hawkins; Clyde B. Simpson, Jr., both of Jacksonville, Fla.; Gustave J. Klein, Great Neck, N.Y.

[73] Assignee: Revlon Consumer Products Corporation, New York, N.Y.

[21] Appl. No.: 896,525

[22] Filed: Jun. 9, 1992

[51] Int. Cl.$^5$ .................................................. A61K 7/06

[52] U.S. Cl. .................................... 132/202; 132/204; 424/71; 424/72

[58] Field of Search ............... 132/203, 204, 205, 206; 424/71, 72

[56] References Cited

U.S. PATENT DOCUMENTS

| | | | |
|---|---|---|---|
| 4,228,810 | 10/1980 | Moore et al. | 13/204 |
| 4,798,722 | 1/1989 | Edman et al. | 424/71 |
| 4,947,878 | 8/1990 | Crews | 132/203 |
| 5,077,042 | 12/1991 | Darkwa | 424/71 |

OTHER PUBLICATIONS

Cosmetics & Toiletries, vol. 106, Jul. 1991, pp. 49-51.
Cosmetics & Toiletries, vol. 94, Apr. 1979, pp. 51-56.

*Primary Examiner*—Gene Mancene
*Assistant Examiner*—Frank A. LaViola
*Attorney, Agent, or Firm*—Julie Blackburn

[57] ABSTRACT

A method for determining the effectiveness of hair relaxer treatments immediately after treatment, and a method for determining the amount of curl reversion at specified time periods after relaxer treatment.

12 Claims, No Drawings

METHOD FOR DETERMINING EFFECTIVENESS OF RELAXER TREATMENT

TECHNICAL FIELD

The invention is in the field of methods for determining the effectiveness of hair treatments.

BACKGROUND OF THE INVENTION

Hair relaxers or straighteners are very popular today and widely used by individuals desiring to straighten very curly or kinky hair.

There are a variety of hair relaxers available commercially, and some are better than others for achieving the desired straightening of the hair. In addition, formulators are constantly searching for ways to improve hair relaxing treatments.

Often, however, the degree of improvement offered by a new or different formulation is difficult to determine because no objective standard has been developed to assess effectiveness. Instead relaxer effectiveness is determined based upon rating schemes wherein the beautician performing the procedure assesses the degree of relaxer effectiveness by rating the hair according to one of several types of scales. This method is useful but not entirely precise due to the subjectivity of the beautician who analyzes the hair.

Accordingly there is a need for a precise, accurate method for evaluating the effectiveness of a hair relaxing treatment.

SUMMARY OF THE INVENTION

The invention is directed to a method for determining the effectiveness of a hair relaxer treatment ("Method I") comprising the steps of:

a) Cutting a representative sample of hair from the subject's head prior to relaxer treatment, b) Gently stretching the hair til straight and cutting a sample of a predetermined length, c) allowing the hair sample of (b) to contract to its natural configuration and measuring the length, d) treating the subject's hair with relaxer, e) cutting a representative sample of hair from the subject's head after relaxer treatment, f) gently stretching the hair til straight and cutting a sample of the same predetermined length as in (b), g) allowing the hair sample of (f) to contract to its natural configuration and measuring the length, h) determining the percent relaxation according to the formula:

$$\%\ \text{relaxation} = 100 \times \frac{(\text{length of hair after relaxation } [g]) - (\text{length of hair before relaxation } [b])}{(\text{length of hair } [b])}$$

The invention is also directed to a method for measuring curl reversion in a subject treated according to Method I comprising the steps of:

a) clipping a representative sample of hair from the head of a subject previously treated in accordance with Method I, b) snipping the new hair growth from the sample, c) gently stretching the hair til straight and snipping a sample of the same predetermined length as in (b) of Method I, d) allowing the hair sample of (b) to contract to its natural configuration and measuring the length, e) determining the percent relaxation according to the following formula:

$$\%\ \text{relaxation} = 100 \times \frac{(\text{length of hair after relaxation } [d]) - (\text{length of hair before relaxation } [b \text{ of Method I}])}{(\text{length of hair } [c])}$$

DETAILED DESCRIPTION

The term "hair relaxer effectiveness" means the ability of a hair relaxer to relax or straighten curly or kinky hair. A relaxer is generally considered effective in straightening the hair if it results in 10–100% relaxation according to the above formula.

The method of the invention can be used to assess the effectiveness of any hair relaxer treatment, including those which are commercially available, as well as those which are in experimental stages.

The first step of the process involves obtaining samples of the subject's hair prior to the relaxation treatment. Hair samples which are representative of the hair in general should be selected. It is suggested that the sample be obtained by snipping the hair as close as possible to the scalp.

After the hair sample is obtained, it is important to cut a portion of the sample to a predetermined length. The sample is gently stretched by, for example, clamping one end with a hair clamp or the like. The other end of the sample is grasped in a suitable grasping means such as a hemostat. The hair sample is gently stretched so that it is straight. A sample of the desired length is then cut. Generally a hair sample of about 0.5 inches is most desirable for the test of the invention, although samples ranging from 0.2–1.0 inches are suitable. It is important that this sample measurement be as exact as possible, and to ensure that the measurement is taken while the hair is completely straight. The measurement is recorded.

In the next step, the hair is allowed to fall to a suitable surface such as a filter paper or the like, and assume its natural configuration. The length of the dry hair in its natural configuration is then measured and recorded. The test of the invention is preferably conducted on dry hair. However, the relaxation process involves chemically breaking the disulfide bonds in the hair fiber protein and causing them to reorient into the desired "straight" configuration. It is also known that other bonds such as hydrogen bonds play a role in the relaxation process. By repeating the measurement process for wet hair, the effects of other types of bonds on the relaxation process can be determined. The hair sample may be wet by placing it into a petri dish with water, or the like. The measurement of the wet hair in its natural configuration is taken within 10–15 seconds while the hair is in the water. Wet hair generally contracts so it is expected that when measuring the same sample of wet and dry hair, the wet sample will be somewhat shorter than the dry sample when both samples are allowed to assume their natural unrelaxed configurations.

After both hair measurements are recorded the relaxer treatment of choice is applied to the subject's hair. It may be desired to do "half heads" if an experimental relaxer treatment is being compared to a control. Doing "half heads" is a very common practice in experimental situations. In this case a control composition is applied to one half of the subject's head while the experimental composition is applied to the other half of the subject's head. At the end of both treatments the hair on one half of the head is compared with the hair on the other half of the head. If half heads are done using the method of the invention, then it is important that the hair samples be taken from both sides of the head so that before and after relaxation effectiveness measurements for both the control and test sides are available.

Most relaxer treatments are completed by washing the hair with an acidic shampoo having a pH range of 4.0–6.0. The acidic shampoo acts to neutralize the bases used in the relaxation treatment. After the shampoo step the hair is towelled dry.

A second hair sample is taken from the subject's head after completion of the relaxer treatment. The sample is taken in the same manner as the sample obtained prior to treatment, namely a small portion of hair which is representative of the relaxed hair in general is snipped off at the scalp. If half heads were done, then a sample must be taken from both sides of the head.

One end of the hair sample is clamped to hold it in a fixed position. The other end of the sample is grasped in a suitable device such as a hemostat. The hair is gently stretched so that it is straight. A sample of the same length as the sample cut prior to relaxation is clipped. For example if a 0.5 inch sample of hair was obtained prior to relaxation, it is essential that the sample obtained after relaxation is 0.5 inches. The sample is then allowed to fall to a surface and assume its natural configuration. The length of the sample in its natural configuration is measured and recorded. If desired the sample is wet in the same manner as before and the measurement repeated on wet hair.

The percent relaxation is calculated according to the following formula:

$$\%\ \text{relaxation} = 100 \times \frac{(\text{length of hair after relaxation}) - (\text{length of hair before relaxation})}{(\text{length of hair sample cut})}$$

In the above formula, the term "length of hair after relaxation" means the length of the hair sample in its natural configuration. For example, a 0.5 inch hair sample was obtained by clamping one end of the hair sample in a clamp and using a hemostat to grasp the other end of the hair and pull it gently straight. A 0.5 inch section was cut (length of hair sample cut). The 0.5 inch sample was allowed to fall to a surface and assume its natural configuration and a second measurement of length (0.25 inch) was obtained (length of hair before relaxation). After relaxation treatment a second representative sample of 0.5 inch was obtained from the head of the subject according to the procedure set forth above. The 0.5 inch sample was allowed to fall to a flat surface and the length was measured (0.45 inch) (length of hair after relaxation). The percent of relaxation was calculated as follows:

$$\%\ \text{relaxation} = 100 \times \frac{0.45 - 0.25}{0.50} = 40\%\ \text{relaxation}$$

The procedure of the invention lends itself well to comparing test and experimental hair relaxation methods. In the case where half heads are done, the % relaxation can be calculated and compared for both experimental and control sides to provide an indication of the effectiveness of one treatment vs. another.

The method of the invention provides a simple, effective, objective way to evaluate the effectiveness of hair relaxer treatments.

The invention is also directed to a method of evaluating "curl reversion". This term means the amount of reversion to the natural curly state exhibited by hair which has been previously treated with relaxer. In order to test curl reversion, the subject whose hair relaxer treatment has been quantified in accordance with Method I is asked to return for further analysis at a desired period of time after the initial relaxation treatment. Generally two to three weeks after the initial treatment is preferred, since this time period provides a good indication of the effectiveness of the relaxer treatment over time.

A hair sample is obtained from this subject by snipping a sample representative of the hair in general beginning at the scalp. Depending on the amount of time which has elapsed between the first relaxer treatment and the return visit, the appropriate amount of hair is snipped off the scalp end of the sample. For example, if the subject is asked to return two to three weeks after the initial relaxation treatment, it can be assumed that about ¼ inch of new hair has grown since that time. Thus, ¼ inch of hair is snipped from the end of the sample taken from the scalp area. This ¼ inch represents the unrelaxed new growth and its removal is essential to the accuracy of the method.

After removing the new growth, one end of the hair sample is clamped to secure it. The other end of the sample is grasped in a hemostat or other suitable instrument. The sample is gently stretched. A hair sample of the desired length is snipped. It is essential that this hair sample be of the same length as the sample obtained from this same model in the before and after relaxation procedures of Method I. For example, if the hair sample obtained on this subject was 0.5 inches pursuant to Method I, then the hair sample obtained on this subject when tested two to three weeks later should also be 0.5 inches.

The hair sample is then allowed to fall to a flat surface and assume its natural configuration. The sample length is measured again and the measurement recorded. The percent relaxation remaining after elapse of the time period between the quantification of Method I and the subject's second visit is determined according to the following formula:

$$\%\ \text{relaxation} = 100 \times \frac{(\text{length of hair after relaxation/second visit}) - (\text{length of hair before relaxation/Method I})}{(\text{length of hair sample cut})}$$

For example, take the subject used to illustrate Method I supra. If the length of a 0.5 inch section of this subject's hair at this second visit was 0.40 inches, the % relaxation would be calculated as follows:

$$\%\ \text{relaxation} = 100 \times \frac{0.40 - 0.25}{0.50} = 30\%$$

As can be seen from the above illustration, the hair exhibits 30% relaxation after two to three weeks. Compare this with 40% relaxation achieved immediately after the relaxation treatment. The difference between 30 and 40% is the amount of curl reversion. In this case the curl reversion is 10%.

The method of the invention was used to test and compare the effectiveness of a novel relaxer formulation which is the subject matter of copending patent application Case Docket Rev 92-6, entitled "Hair Relaxer Composition and Associated Methods", which is filed on the same day as this application and which is hereby incorporated by reference.

The invention will be further described in connection with the following examples which are set forth for the purposes of illustration only.

EXAMPLE 1

An experimental hair relaxer (hereinafter referred to as "Relaxer 2000") was compared with a commercial lye based relaxer referred to as LYE The formula of the Relaxer 2000 base composition is set forth below:

| | w/w % |
|---|---|
| Stearyl alcohol | 14.00 |
| PEG-75 lanolin | 4.00 |
| Petrolatum | 18.00 |
| Polawax | 5.50 |
| Paraffin | 1.50 |
| Propylene glycol | 5.00 |
| Hydrolyzed animal protein | 5.00 |
| Stearic acid | 1.50 |
| Sodium hydroxide (50%) | 6.50 |
| Water | 38.70 |
| Fragrance | 0.30 |

Approximately 250 grams of the base composition of Example 1 was mixed with about 50 grams of the following additive composition:

| | w/w % |
|---|---|
| Octoxynol-1 | 25.00 |
| Oleyl Alcohol | 9.70 |
| Mineral oil | 30.00 |
| PEG-75 lanolin | 4.00 |
| Methylparaben | 0.20 |
| Propylparaben | 0.10 |
| Butylparaben | 0.10 |
| Fragrance | 0.30 |
| Water | 30.6 |

EXAMPLE 2

The LYE control relaxer was of the following formula:

| | w/w % |
|---|---|
| Petrolatum | 13.50 |
| Polawax | 12.50 |
| Hexylene glycol | 5.50 |
| Hydrolyzed animal protein | 0.20 |
| NaOH | 2.12 |
| Water | 42.78 |
| Fragrance | 0.40 |
| Mineral oil | 13.50 |

EXAMPLE 3

The method of the invention was employed in comparatively testing the relaxer compositions of Examples 1 and 2 above as follows:

1. Before applying relaxer, representative samples of hair from both the right and left side of the subject's head were obtained by snipping a small portion of hair that looked representative of the hair sample in general. The sample was obtained by snipping the hair as close as possible to the scalp.

2. One end of the sample was placed in a clamp or other device to secure it. The other end of the sample was grasped in a hemostat and pulled gently til straight between the clamp and the hemostat. A 0.5 inch section of hair was cut, ensuring that the small amount of hair clamped within the hemostat was included within this 0.5 inch measurement.

3. The hair clipping was released and allowed to fall onto white paper. The length of the hair in the natural unrestrained configuration was measured and recorded.

4. This hair clipping was then wet by placing into a petri dish containing water for a few seconds. The length of the clipping was measured within 10–15 seconds while in the water and recorded.

5. The beautician then determined whether the subject's hair was porous, nonporous, or of medium porosity according to methods well known to skilled beauty technicians. One half of each model's head was treated with Relaxer 2000 which comprised a mixture of 250 grams of the base composition of Example 1 and 50 grams of the additive composition of Example 1. The other half of the subject's head was treated with LYE (the lye based relaxer of Example 2). The relaxer compositions were left on the head for 13–26 minutes, depending on the porosity of the subject's hair. For example, the relaxer was left on the head from 13–17 minutes if the subject's hair was porous, 18–22 minutes if the hair was of medium porosity, and 23–26 minutes if the hair was nonporous.

6. After expiration of the appropriate time period, each subject's hair was washed with a conditioning shampoo of pH 4.0–6.0, namely Herbal Deep Clean.

7. Test samples were again taken on the left and right sides of the head in accordance with (1) and (2) above. The length of each clipping was measured dry and then wet in accordance with (3) above. The percentage of full relaxation was calculated for both wet and dry samples as follows:

$$\% \text{ relaxation} = 100 \times \frac{(\text{length of hair after relaxation}) - (\text{length of hair before relaxation})}{(\text{length of hair sample cut})}$$

The measurements are as follows:

| Hair length measurements before relaxation on dry hair | | Hair length measurements after relaxation on dry hair | |
|---|---|---|---|
| 2000 | LYE | 2000 | LYE |
| 0.399 | 0.373 | 0.500 | 0.500 |
| 0.383 | 0.442 | 0.428 | 0.420 |
| 0.289 | 0.270 | 0.488 | 0.500 |
| 0.158 | 0.196 | 0.487 | 0.314 |
| 0.265 | 0.295 | 0.355 | 0.207 |
| 0.398 | 0.372 | 0.500 | 0.500 |
| 0.320 | 0.365 | 0.488 | 0.482 |
| 0.407 | 0.370 | 0.480 | 0.437 |
| 0.362 | 0.395 | 0.410 | 0.399 |
| 0.407 | 0.405 | 0.486 | 0.471 |

-continued

| | | | |
|---|---|---|---|
| 0.377 | 0.358 | 0.500 | 0.435 |
| 0.179 | 0.241 | 0.357 | 0.322 |
| 0.390 | 0.359 | 0.402 | 0.327 |
| Average Length in Inches | | | |
| 0.333 | 0.338 | 0.452 | 0.409 |
| 0.083 | 0.073 | 0.053 | 0.088 SD |
| 0.285 | 0.294 | 0.420 | 0.356 |
| to | to | to | to 95% |
| 0.383 | 0.382 | 0.484 | 0.462 |
| % Relaxation based on 95% confidence level | | | |
| 57 to 77 | 59 to 76 | 84 to 97 | 71 to 92 |

| Hair length measurements before relaxation on wet hair | | Hair length measurements after relaxation on wet hair | |
|---|---|---|---|
| 2000 | LYE | 2000 | LYE |
| 0.353 | 0.296 | 0.500 | 0.496 |
| 0.316 | 0.398 | 0.428 | 0.420 |
| 0.200 | 0.196 | 0.468 | 0.500 |
| 0.148 | 0.174 | 0.487 | 0.282 |
| 0.321 | 0.277 | 0.313 | 0.196 |
| 0.369 | 0.354 | 0.490 | 0.487 |
| 0.276 | 0.334 | 0.415 | 0.455 |
| 0.359 | 0.370 | 0.462 | 0.432 |
| 0.316 | 0.378 | 0.395 | 0.359 |
| 0.380 | 0.373 | 0.481 | 0.464 |
| 0.352 | 0.318 | 0.492 | 0.429 |
| 0.169 | 0.234 | 0.305 | 0.312 |
| 0.360 | 0.295 | 0.402 | 0.300 |
| Average Length in Inches | | | |
| 0.301 | 0.307 | 0.434 | 0.395 |
| 0.076 | 0.069 | 0.063 | 0.092 SD |
| 0.255 | 0.265 | 0.395 | 0.359 |
| to | to | to | to 95% |
| 0.347 | 0.349 | 0.471 | 0.451 |
| % Relaxation based on 95% confidence level | | | |
| 51 to 69 | 53 to 70 | 79 to 94 | 68 to 90 |

SD means Standard Deviation
95% means 95% confidence level

The above method provides an easy method for comparing the effectiveness of an experiment vs. control hair relaxer treatment process.

EXAMPLE 4

The models whose hair was relaxed in Example 3 were asked to return to the salon two to three weeks after the initial procedure in order to determine the degree to which hair reverted to its natural curly state after two to three weeks. The following test method for determining curl reversion was employed.

1. Test samples of dry hair were obtained from the right and left side of each model's head by snipping representative samples beginning at the scalp.

2. Hair regrowth of ¼ inch was assumed in the two to three week period so ¼ inch of the hair sample taken from nearest the scalp was snipped off.

3. A 0.5 inch section of hair was cut by clamping on end of the hair sample in a clamp or other securing device. The other end of the sample was grasped in a hemostat and pulled gently til straight. A 0.5 inch section was cut.

4. The length of the hair was measured in its natural state and the percent of full relaxation calculated in accordance with the formula of (7) in Example 8.

5. The measuring process was repeated with wet hair and the percent of full relaxation calculated again.

6. The % relaxation figure from Example 8 was compared with the % relaxation for the same model 2-3 weeks after treatment.

| Hair length measurements | Hair length measurements |
|---|---|

-continued

| after relaxation on dry hair | | 2-3 wks later on dry hair | |
|---|---|---|---|
| 2000 | LYE | 2000 | LYE |
| 0.500 | 0.500 | 0.500 | 0.500 |
| 0.488 | 0.500 | 0.494 | 0.490 |
| 0.487 | 0.314 | 0.500 | 0.492 |
| 0.355 | 0.207 | 0.466 | 0.470 |
| 0.488 | 0.482 | 0.495 | 0.476 |
| 0.410 | 0.399 | 0.395 | 0.471 |
| 0.486 | 0.471 | 0.500 | 0.490 |
| 0.500 | 0.435 | 0.500 | 0.497 |
| 0.357 | 0.322 | 0.462 | 0.389 |
| Average Length in Inches | | | |
| 0.457 | 0.413 | 0.481 | 0.454 |
| 0.056 | 0.096 | 0.032 | 0.071 SD |
| 0.417 | 0.344 | 0.458 | 0.403 |
| to | to | to | to 95% |
| 0.497 | 0.482 | 0.504 | 0.505 |
| % Relaxation based on 95% confidence level | | | |
| 83 to 99 | 69 to 96 | 92 to 101 | 80 to 101 |

| Hair length measurements after relaxation on wet hair | | Hair length measurements 2-3 wks later on wet hair | |
|---|---|---|---|
| 2000 | LYE | 2000 | LYE |
| 0.500 | 0.496 | 0.500 | 0.500 |
| 0.468 | 0.500 | 0.475 | 0.476 |
| 0.487 | 0.282 | 0.498 | 0.489 |
| 0.313 | 0.196 | 0.442 | 0.458 |
| 0.490 | 0.487 | 0.485 | 0.236 |
| 0.415 | 0.455 | 0.486 | 0.476 |
| 0.395 | 0.359 | 0.388 | 0.456 |
| 0.481 | 0.464 | 0.500 | 0.494 |
| 0.305 | 0.312 | 0.418 | 0.389 |
| Average Length in Inches | | | |
| 0.435 | 0.398 | 0.469 | 0.446 |
| 0.071 | 0.099 | 0.037 | 0.076 SD |
| 0.384 | 0.327 | 0.443 | 0.392 |
| to | to | to | to 95% |
| 0.486 | 0.496 | 0.495 | 0.500 |
| % Relaxation based on 95% confidence level | | | |
| 77 to 97 | 65 to 99 | 89 to 99 | 78 to 100 |

The above results demonstrate the relaxer of the

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A method for determining the effectiveness of a hair relaxer treatment comprising the steps of:

a) Cutting a representative sample of hair from a subject's head prior to relaxer treatment, b) Gently stretching the hair until straight and cutting a sample of a predetermined length, c) allowing the hair sample of (b) to contract to its natural configuration and measuring the length, d) treating the subject's hair with relaxer, e) cutting a representative sample of hair from the subject's head after relaxer treatment, f) gently stretching the hair until straight and cutting a sample of the same predetermined length as in (b), g) allowing the hair sample of (f) to contract to its natural configuration and measuring the length, h) determining the percent relaxation according to the formula:

$$\% \text{ relaxation} = 100 \times \frac{(\text{length of hair after relaxation } (g)) - (\text{length of hair before relaxation } (b))}{(\text{length of hair } (b))}$$

2. The method of claim 1 wherein the predetermined length of hair is 0.5 inches.

3. The method of claim 1 wherein said method is performed with dry hair.

4. The method of claim 1 wherein said method is performed with wet hair.

5. The method of claim 1 wherein an experimental relaxer composition is applied to one half the subject's head and a control relaxer composition is applied to the other half of the subject's head.

6. The method of claim 1 wherein the hair is stretched by placing one end in a clamp and grasping the other end with a hemostat.

7. The method of claim 5 wherein the % relaxation is determined for both the experimental and control sides of the subject's head.

8. A method for measuring curl reversion in a subject treated according to claim 1 further comprising the steps of:

i) cutting a representative sample of hair from the head of the subject previously treated with relaxer, j) snipping new hair growth from the sample, k) gently stretching the hair until straight and cutting a sample of the same predetermined length as in step (b), l) allowing the hair sample of (j) to contract to its natural configuration and measuring the length, m) determining the percent relaxation according to the following formula:

$$\% \text{ relaxation} = \frac{100 \times (\text{length of hair after relaxation } (l)) - (\text{length of hair before relaxation } (b))}{(\text{length of hair } (k))}$$

9. The method of claim 8 wherein two to three weeks has elapsed since the relaxer treatment.

10. The method of claim 9 wherein the predetermined length of hair clipped is 0.5 inches.

11. The method of claim 10 wherein ¼ inch of new growth is removed from the hair sample.

12. The method of claim 11 wherein the hair is gently stretched by clamping one end of the sample in a clamp and grasping the other end of the sample with a hemostat.

* * * * *